(12) United States Patent
Verzijl et al.

(10) Patent No.: US 8,088,954 B2
(45) Date of Patent: Jan. 3, 2012

(54) PREPARATION OF A SATURATED ALDEHYDE

(75) Inventors: Gerardus Karel Maria Verzijl, AR Well (NL); Henricus Martinus Maria Gerardus Straatman, LG Horst (NL); Andreas Hendrikus Maria De Vries, CR Maastricht (NL); Lizette Schmieder, AB Haelen (NL); Jeroen Antonius Franciscus Boogers, JK Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/668,232

(22) PCT Filed: Jul. 11, 2008

(86) PCT No.: PCT/EP2008/059144
§ 371 (c)(1),
(2), (4) Date: Apr. 5, 2010

(87) PCT Pub. No.: WO2009/007461
PCT Pub. Date: Jan. 15, 2009

(65) Prior Publication Data
US 2010/0197972 A1   Aug. 5, 2010

(30) Foreign Application Priority Data

Jul. 11, 2007  (EP) .................................. 07013561

(51) Int. Cl.
C07C 47/105   (2006.01)
C07C 45/67    (2006.01)
C07C 41/18    (2006.01)
(52) U.S. Cl. ......... 568/427; 568/442; 568/648; 568/649
(58) Field of Classification Search .................. 568/427, 568/442, 648, 649
See application file for complete search history.

(56) References Cited

U.S. PATENT DOCUMENTS 6,683,206 B2 *  1/2004  Stutz et al. .................... 562/465
6,881,868 B2 *  4/2005  Stutz et al. .................... 568/608

FOREIGN PATENT DOCUMENTS

| EP | 0 678 503 | 10/1995 |
| WO | 02/02487 | 1/2002 |
| WO | 02/02500 | 1/2002 |

OTHER PUBLICATIONS

International Search Report for PCT/EP2008/059144, mailed Aug. 26, 2008.
Written Opinion of the International Searching Authority for PCT/EP2008/059144, mailed Aug. 26, 2008.

* cited by examiner

*Primary Examiner* — Sikarl Witherspoon
(74) *Attorney, Agent, or Firm* — Nixon & Vanderhye P.C.

(57) ABSTRACT

The invention relates to a compound according to Formula (IX) and salts thereof, wherein $R_1$, $R_2$ and $R_5$ are each independently selected from H and hydrocarbon moieties, which hydrocarbon moieties optionally comprise one or more heteroatoms, and which hydrocarbons optionally comprise substituents, or when the compound according to formula (IX) is a salt, $R_1$ and/or $R_2$ may be a cation, $R_3$, and $R_4$ each independently selected from hydrocarbon moieties, which hydrocarbon moieties optionally comprise one or more heteroatoms, and which hydrocarbons optionally comprise substituents, and wherein any two of $R_1$, $R_2$, $R_3$, $R_4$ and $R_5$ are optionally linked together to form a ring structure. The invention further relates to the preparation of such a compound and to the use of such a compound for preparing a pharmaceutical compound, an agrochemical compound, an intermediate for a pharmaceutical compound or an intermediate for an agrochemical compound.

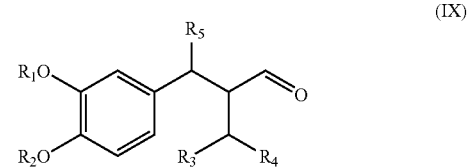

(IX)

5 Claims, No Drawings

PREPARATION OF A SATURATED ALDEHYDE

This application is the U.S. national phase of International Application No. PCT/EP2008/059144, filed 11 Jul. 2008, which designated the U.S. and claims priority to European Application No. 07013561.1, filed 11 Jul. 2007, the entire contents of each of which are hereby incorporated by reference.

The invention relates to a novel aldehyde, to a method for preparing such an aldehyde and to the use of such an aldehyde as an intermediate compound for the preparation of a pharmaceutical or agrochemical.

It is known that δ-amino-γ-hydroxy-ω-aryl-octanoyl-amides exhibit pharmaceutical activity, as described in EP-A-0678503. In particular such compounds have been described to exhibit antihypertensive activity. Such compounds can be prepared from substituted 2-alkyl-3-phenyl-1-propanols. The preparation of such an alcohol is described in WO 02/02487. The described method requires a plurality of steps. First an aldol reaction is performed between a substituted benzaldehyde and an aliphatic ester to form the Aldol product. The Aldol-product is isolated and only thereafter the hydroxide is converted into a leaving group. Next, an α,β-unsaturated carboxylic ester is formed in the presence of a strong base. In a further reaction step the carboxylic ester is reduced to form an unsaturated alcohol. The unsaturated alcohol is hydrogenated in yet another step making use of an asymmetric hydrogenation catalyst.

It is a drawback of the method described in WO 02/02487 that the aldol-product needs to be isolated and the hydroxide group thereof converted into a leaving group before forming the unsaturated carboxylic acid ester. Further, the yield of the desired isomer is relatively low (about 57%, starting from the aldehyde). The anti-diastereomer is removed without further use. Moreover, the plurality of reaction steps may make the process complicated.

It is an object of the present invention to provide a novel compound which is useful for preparing a pharmaceutical, an intermediate for a pharmaceutical, or an intermediate for an Agrochemical, in particular a compound suitable for preparing a δ-amino-γ-hydroxy-ω-aryl-octanoyl-amide or a substituted 2-alkyl-3-phenyl-1-propanol compound suitable for preparing such octanoyl-amide.

It is in particular an object to provide such a compound which can be used in a method for preparing a substituted 2-alkyl-3-phenyl-1-propanol (a compound according to Formula (II)), which method overcomes one or more problems associated with a prior art process such as described above.

One or more objects which may be solved in accordance with the invention will become apparent from the description and/or claims, below.

It has now been found that one or more objects are achieved by providing a specific aldehyde. Accordingly, the present invention relates to a compound according to Formula (IX) and salts thereof,

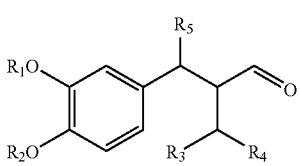

(IX)

wherein $R_1$ and $R_2$ are each independently selected from H and hydrocarbon moieties, which hydrocarbon moieties optionally comprise one or more heteroatoms, and which hydrocarbons optionally comprise substituents, or when the compound according to formula (IX) is a salt, $R_1$ and/or $R_2$ may be a cation, $R_3$, and $R_4$ each independently selected from hydrocarbon moieties, which hydrocarbon moieties optionally comprise one or more heteroatoms, and which hydrocarbons optionally comprise substituents and $R_5$ is selected from H and hydrocarbon moieties, which hydrocarbon moieties optionally comprise one or more heteroatoms, and which hydrocarbons optionally comprise substituents, and wherein any two of $R_1$, $R_2$, $R_3$, $R_4$ and $R_5$ are optionally linked together to form a ring structure. In an embodiment of the invention $R_3$ and $R_4$ each independently are selected from the group of $C_1$-$C_6$ alkyl and $R_5$ is selected from H, $C_1$-$C_6$ alkoxyls, tri($C_1$-$C_6$ alkyl)silyls, $C_1$-$C_6$ alkyls, and $R_1$ and $R_2$ are optionally linked together to form a ring structure.

Within the context of the present invention the term "hydrocarbon" is meant to include substituted and unsubstituted hydrocarbons, hydrocarbons with one or more heteroatoms (such as S, N, O, P, Cl, Br, F, I, Si) and hydrocarbons without heteroatoms, unless specifically mentioned otherwise. A hydrocarbon group of a compound, e.g. $R_3$, $R_4$ or $R_5$ in Formula (IX) or another Formula included herein, can optionally contain a heteroatom, in particular O, S, N or Si, at the position at which the group is bound to the remainder of the compound, e.g. a hydrocarbon group can be an alkoxyl, aryloxyl, sulphoxyl or an organo-silicon group, for instance an trialkylsilyl. The hydrocarbon may comprise a linear or a branched structure, such as a linear or branched alkyl or alkenyl. The hydrocarbon may comprise one or more rings, which rings optionally contain one or more heteroatoms, in particular one or more heteroatoms selected from N and O. The ring may be aliphatic (cycloalkyl) or aromatic (aryl). The hydrocarbon may also be an oxygen protective group. The hydrocarbon, such as the optionally substituted alkyl, optionally substituted cycloalkyl, optionally substituted aryl or optionally substituted alkylaryl, may in particular comprise 1-20 carbon atoms in total, more in particular 1 to 12 or 1 to 6 carbon atoms. In case of the hydrocarbon comprises a ring, the number of carbon atoms usually is at least 3.

In case the compound according to formula (IX) is a salt, $R_1$ and/or $R_2$ may be a cation. Suitable cations are all monovalent cations and cations having a higher valency. In this case, $R_1$ and/or $R_2$ are preferably selected from the group of $Na^+$, $Li^+$, $K^+$ and $Ca^{2+}$.

Any two of $R_1$, $R_2$, $R_3$, $R_4$ and $R_5$ are optionally linked together to form a ring structure. In particular $R_1$ and $R_2$ may be linked together to form a ring structure and/or $R_3$ and $R_4$ may be linked together to form a ring structure. For example, $R_1$, and $R_2$ together are —$CH_2$—, thereby forming a five-membered ring.

$R_1$ may in particular be hydrogen, 3-methoxy-propyl or an oxygen protective group. $R_2$ may in particular be hydrogen, $C_1$-$C_6$ alkyl, preferably methyl, or an oxygen protective group.

Within the context of the present invention the term "oxygen protective group" is used to describe any group suitable to protect an oxygen of an alcohol against an undesired reaction. In particular, the oxygen protective group may be selected from the group of tosylate, mesylate, benzoylate, benzoate, trimethylsilyl and organic acid residues, for instance acetate.

$R_3$ and/or $R_4$ may in particular be selected from $C_1$-$C_6$ alkyl, $C_1$-$C_6$ alkenyl, such as allyl, and unsubstituted or substituted phenyl. Most preferably, $R_3$ and/or $R_4$ are methyl.

$R_5$ may in particular be selected from H, and $C_1$-$C_6$ alkoxyls, tri($C_1$-$C_6$ alkyl)silyls, $C_1$-$C_6$ alkyls, more in particular from $C_1$-$C_6$ alkyls and H. $R_5$ preferably is H.

Preferred compounds according to the invention are:
- 2-(3-(3-methoxypropoxy)-4-methoxybenzyl)-3-methylbutanal,
- 2-(3-(3-methoxypropoxy)-4-hydroxybenzyl)-3-methylbutanal,
- 2-(3-methoxypropoxy)-4-(2-formyl-3-methylbutyl)phenyl tolylsulfonate,
- 2-(3-methoxypropoxy)-4-(2-formyl-3-methylbutyl)phenyl benzoate,
- 2-(3,4-dihydroxybenzyl)-3-methylbutanal, and
- 2-(3-trimethylsilylhydroxy)-4-methoxybenzyl)-3-methylbutanal.

The compound according to the invention usually contains at least one stereogenic center, in particular the compound may comprise one or two stereogenic centers. The compound may be provided as a racemic mixture, a diastereomeric mixture, or be scalemic i.e. enantio-enriched (i.e. one of the enantiomers is formed in excess of the other but not to the exclusion of the other) or enantiopure (i.e. essentially only one of the enantiomers is formed). Thus, the compound may be the 2(S), 3(S) diastereomer, 2(S), 3(R) diastereomer 2(R), 3(S) diastereomer, 2(R), 3(R) diastereomer or a mixture thereof.

The invention further relates to a method for preparing a compound according to Formula (IX), comprising converting, in particular by reduction or hydrogenation, the α-β carbon-carbon unsaturation of an E-isomer, a Z-isomer or a mixture of an E-isomer and a Z-isomer of a compound according to Formula (I)

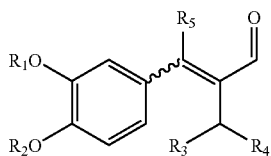
(I)

wherein $R_1$, $R_2$, $R_3$ and $R_4$ and $R_5$ are as defined in claim 1, to form the compound of Formula (IX).

The aldehyde of Formula I can be prepared by converting a benzaldehyde represented by Formula (III)

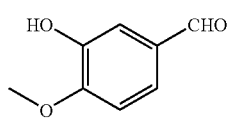
(III)

optionally comprising an oxygen protective compound on the phenolic OH to obtain a compound with Formula (IV)

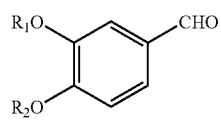
(IV)

wherein $R_1$ and $R_2$ are as identified above and react the compound of Formula (IV) with an aldehyde with Formula (V) or an enamine thereof

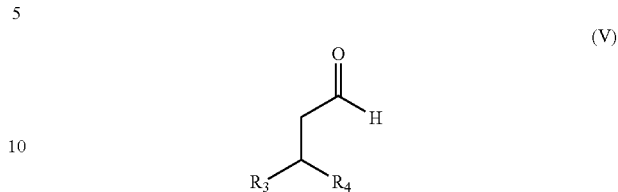
(V)

(wherein $R_3$ and $R_4$ are as defined above).

It is also possible to prepare an aldehyde of the Formula (I) by reacting a corresponding benzaldehyde represented by Formula (VI)

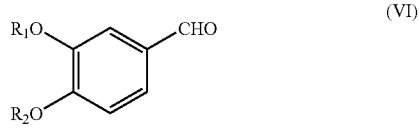
(VI)

wherein $R_1$ may in particular be a 3-Methoxypropyl or an oxygen protective group and $R_2$ may in particular be a hydrocarbon, preferably alkyl or H, with an aldehyde of Formula (V)

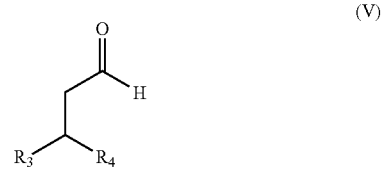
(V)

wherein $R_3$ and $R_4$ are as defined above, or the corresponding enamine of the aldehyde (V), to obtain an aldehyde with Formula (VII)

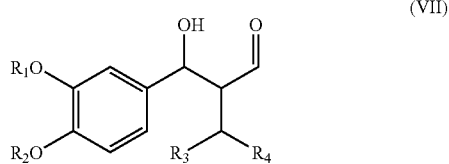
(VII)

Next, the aldehyde of Formula (VII) can be converted in a aldehyde according to Formula (I) by acidic, or alkaline elimination.

The conversion of a compound according to Formula (I) to a compound of Formula (IX) may conveniently be carried out with hydrogen gas, in the presence of a hydrogenation catalyst, or another hydrogen source, e.g. isopropanol, formic acid, Hantzsch ester, NADPH, or NADH, in the presence of a catalyst or a metal hydride.

Preferably, the conversion of a compound according to Formula (I), which may be an E-isomer, A Z-isomer or a mixture thereof, into a compound according to Formula (IX) is preformed enantioselectively with respect to the (R)-enantiomer or the (S)-enantiomer. More preferably, the (R)-enantiomer is formed in excess of the (S)-enantiomer.

The catalyst used in accordance with the invention may in principle be any catalyst capable of catalysing the reduction of the α,β unsaturation of the compound of Formula (I) of any of the E or Z isomers, or both.

In an embodiment, the catalyst is an organocatalyst capable of catalyzing the conversion in the presence of a suitable hydrogen source. A suitable organocatalyst is described in Angew. Chemie 2005, 44, 108-110.

In an embodiment, the catalyst is an enzyme capable of catalyzing the conversion, in the presence of a suitable hydrogen source. Particularly suitable is an enzyme being an oxidoreductase (EC class 1). Preferably, a reductase is used, more preferably an ene reductase (E.C.1.3.1.x) is used, in particular an enone reductase, an enal reductase or an enoate reductase. In principle any such enzyme may be used, e.g., any enzyme described in Fardelone et al., J. Mol. Catal. B: Enzymatic 29 (2004) 41-45; Ferraboschi et al., Tetrahedron: Asymmetry 10(1999) 2639; Mano et al., Plant & Cell Physiology, 43(12):1445-1455 (2002); Hall et al., Angewandte Chemie 2007, 46, 3934-3937. Preferred reductases include old yellow enzymes [EC 1.3.1.x]. Particular preferred are such enzymes from yeasts (OYE, OYE2, OYE3, HYE1, HYE2), from plants (P1) or from mammals (LTB4DH).

The enzyme is preferably used in combination with a suitable cofactor regeneration system for the enzyme. Suitable cofactor regeneration systems are known to those skilled in the art. Examples are the use of formate dehydrogenase combined with formate, or the use of glucose dehydrogenase combined with glucose. The enzyme and the optionally present cofactor regeneration system are used in an effective amount for the desired conversion. Catalytic amounts generally suffice.

Suitable hydrogen sources when using an enzyme, in particular include NADPH (Nicotinamide adenine dinucleotide phosphate) and NADH (Nicotinamide adenine dinucleotide).

The enzyme can be used isolated from an organism, for example in solution or on a carrier, or in an organism, such as a yeast or a bacterium, preferably a bacterium, such as for example E. coli. If desired, the organism can be genetically modified to include a reductase from an other species. In a preferred method, a bacterium, such as E. coli, is used with co-expressed enone reductase and a co-factor regeneration system for the reductase.

In an embodiment, a metal-free organic compound is used, in particular an enantioselective iminium catalyst. Such hydrogenation process may for instance be based on Angew. Chem Int Ed. 2005, 44, 108-110.

In an embodiment the catalyst is a conventional heterogeneous metal catalyst, in particular a transition metal on an inert carrier, e.g. Pd/C, Pt/C, Pd/Al, or Raney Nickel.

In an embodiment, the catalyst is a homogeneous catalyst comprising a transition metal, such as Rhodium, Iridium, Platinum, Palladium, Iron, or Copper, and one or several ligands and optionally additives. The ligands may in particular be selected from the group of phosphines, bisphospines, amines, diamines, aminoalcohols, carbon monoxide, halogens, alkylsulphonates, water soluble ligands, such as water soluble organic acids, e.g. citrate, acetate, $NH_3$.

Optionally, in particular in a method wherein use is made of a metal (ion) complex, the hydrogenation may be carried out in the presence of a ligand promoting asymmetric hydrogenation. In particular, chiral ligands are suitable to promote asymmetric hydrogenation. The ligand may form a complex with the metal or metal ion. Such ligands are e.g. described in WO 06/040096.

In an embodiment, the selective hydrogenation is carried out with a catalyst derived in situ from $Rh_4(CO)_{12}$ and a bisphosphine, e.g. DPPE, or a Rhodium or Iridium based catalyst with tris(m-sulphonyl)phosphine trisodium salt as described in Organometallics, 1991, 10, 2126-2133.

A homogeneous catalyst may be used for asymmetric hydrogenation. Homogeneous asymmetric hydrogenation catalysts are known per se and described for example by John M. Brown in E. Jacobsen, A. Pfaltz, H. Yamamoto(Eds.), Comprehensive Asymmetric Catalysis I to III, Springer Verlag, 1999, pages 121 to 182.

The conversion of the compound according to formula (I) to a compound of formula (IX) may be carried out in the presence of one or more additives, in particular one or more bases, for example amines; in the presence of a quaternary ammonium halogenide (tetrabutylammonium iodide); and/or in the presence of one or more protonic acids, which may be inorganic or organic acids, which accelerate the reaction.

The metal or metal ion complex used as a hydrogenation catalyst is preferably used in quantities from 0.0001 to 10 mol-% based on the compound to be hydrogenated, the range 0.001 to 10 mol-% being especially preferred and the range 0.01 to 5 mol-% being preferred in particular.

The conversion of the compound according to formula (I) to a compound of formula (IX) may be carried out at low or elevated temperatures, in particular at a temperature in the range of −20 to 150° C. Preferably, the temperature is at least 10° C., more preferably at least ambient temperature (for instance about 20° C.). Preferably, the temperature is up 120° C. or less, more preferably 90° C. or less.

The method for the preparation of a compound according to formula (IX) by converting a compound according to formula (I) according to the invention may be carried out at atmospheric pressure or at elevated pressure. In particular the hydrogen pressure, if hydrogen gas is used as a hydrogen source, may be in the range of atmospheric to 200 bars of Hydrogen, more in particular in the range of atmospheric to 50 bars of Hydrogen. The method may be carried out in the absence or the presence of a solvent, wherein one solvent or a mixture of solvents may be used. Suitable solvents include aliphatic, cycloaliphatic and aromatic hydrocarbons (pentane, hexane, petroleum ether, cyclohexane, methylcyclohexane, benzene, toluene, xylene), aliphatic halogenated hydrocarbons(dichloromethane, chloroform, di-and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxan, diethylene glycol monomethyl or monoethyl ether), ketones (acetone, methyl isobutyl ketone), carbonic esters and lactones (ethyl or methyl acetate, valerolactone), N-substituted lactams(N-methylpyrrolidone), carboxamides (dimethylamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water.

In the preparation of a compound according to the invention use may be made of an E-isomer, a Z-isomer or a mixture of an E-isomer and its corresponding Z-isomer, of a compound of Formula (I). The conversion of only one or of both isomers may be accomplished by selecting a suitable catalyst.

The inventors found that by using a catalyst in the method according to the invention for the preparation of a compound according to formula ((IX) under specific reaction conditions an α-β unsaturated compound according to Formula (I) comprising both an E isomer and a Z isomer of the α-β unsaturated compound, both E isomer and Z isomer can be converted in the presence of a hydrogenation catalyst.

In an embodiment, the compound formed is scalemic, i.e. enantio-enriched (i.e. one of the enantiomers is formed in excess of the other but not to the exclusion of the other) or enantiopure (i.e. essentially only one of the enantiomers is formed).

The term "enantioselective" is used to indicate that one of the enantiomers is formed in excess of the other, or even to the exclusion of the other.

As the invention allows conversion of both an E isomer and a Z isomer of an unsaturated compound, the conversion of an isomeric mixture of an E isomer and a Z isomer towards a desired end product is higher than in the known processes wherein only one of the isomers would be converted if such known process would be applied to such a mixture of isomers. It has been found possible to choose conditions such that both E isomer and Z isomer are converted with a good yield. At least for some compounds it has been found possible to substantially completely convert both the E isomer and the Z isomer. As used herein, a conversion is in particular considered substantially complete for a specific isomer if at least 90% of that isomer, in particular at least 95% of that isomer is converted to the compound of the invention. Thus, if desired, a product may be obtained from such mixture, which product is essentially free of the E isomer and the Z isomer, without further purification or after a simpler purification than needed for a product obtained by a known process to obtain a product of similar purity. Moreover, an extra purification step may lead to product loss, and thus reduced overall yield of the product.

If a mixture of isomers of the compound of Formula (I) is used, the mixture usually has a molar ratio of Z isomer to E isomer of 1:99 to 99:1. In particular, the molar ratio of Z isomer to E isomer may be in the range of 5:95 to 95:5, preferably in the range of 10:90 to 90:10, in particular of 20:80 to 80:20, more in particular of 25:75 to 75:25.

The catalyst may be a catalyst that is capable of enantioselectively converting both the E isomer and the Z isomer into the compound of Formula (IX).

The process may further comprise the use of a combination of catalysts, wherein a first catalyst (preferentially) catalyses the conversion of the E isomer and a second catalyst (preferentially) catalyses the conversion of the Z isomer.

The inventors came to the surprising insight that it is also possible to accomplish conversion of both isomers by using a catalyst which until now has only been shown to have substantial catalytic activity towards either the Z isomer or the E isomer, such as a substrate specific catalyst, in particular a substrate specific enzyme. The inventors surprisingly found that in the presence of such a catalyst and a specific reagent, such as a thiol, e.g. thioethanol, conversion of both isomers can be achieved. Without being bound by theory, it is contemplated that the thiol facilitates isomerisation, i.e. transition of Z isomer into the E isomer and/or transition of the E isomer into the Z isomer. It contemplated that such compound reacts with the isomers in a Michael addition and that thereafter a retro-Michael addition reaction takes place, whereby the transition into the other isomer may occur.

Alternatively, or in addition to using such specific reagent, specific reaction conditions, e.g carrying out the reaction in the presence of suitable light, may be used to facilitate isomerisation.

It is in particular surprising that such isomerising reagent can be used in the presence of the catalyst, without unacceptably detrimentally affecting the activity of the catalyst. Thus, there is no need to first transform the isomer that is not or to a lesser extent converted by the catalyst into the active (or more active) isomer, and thereafter in an isolated process step, to reduce the unreacted isomer. Thus, the method according to the invention for the preparation of a compound according to formula (IX) using both E and Z-isomer of a compound according to formula (I) carried out under isomerising conditions can now take place in a one-pot process while at the same time allowing a theoretical yield of 100% to be obtained. Apart from the fact that such process can be employed making use of a simpler reactor system, the isomerisation may take place more efficiently, for example quicker and/or more complete.

Accordingly, in an embodiment of the invention, the method according to the invention is carried out using a mixture of an E-isomer and a Z-isomer represented by Formula I, under isomerising conditions. Isomerising conditions are defined as conditions under which the E and Z isomers of the starting material are converted into each other. Isomerising conditions may be obtained in a variety of ways.

Such conditions may be provided by carrying out the conversion of a compound according to formula (I), in particular a mixture of E- and Z-isomers of the compound according to formula (I) to a compound according to formula (IX), e.g by reduction or hydrogenation, in the presence of a compound capable of participating in a Michael addition and/or retro-Michael addition with the unsaturated compound. Preferably such compound is selected from thiols, including thio-alcohols, alkoxythiols etc; halogens; secondary amines and tertiary amines.

The thiol may for instance be an alkane thiol, e.g., ethane thiol, propane thiol or butane thiol, or an aryl thiol, e.g. thiophenol. In particular, a thio-alcohol may be used as a compound capable of participating in a Michael addition and/or retro-Michael addition. In a preferred embodiment the thio-alcohol is selected from dithiothreythol, 2-hydroxy-1-ethanethiol, hydroxypropane thiol and hydroxybutane thiol.

Of the halogens bromine and iodine, and in particular iodine, are preferred for their handling properties.

The amines may in particular be selected from cyclic secondary amines, dialkylamines and trialkylamines, including substituted cyclic amines, di- and trialkylamines. The alkyl groups of these amines may in particular be a $C_1$-$C_6$ alkyl, more in particular an ethyl or propyl. Pyrrolidine is a suitable cyclic amine.

If used, the compound capable of participating in a Michael addition and/or retro-Michael addition may be used in a catalytic amount, although higher amounts may be used. The molar ratio of said compound capable of participating in a Michael addition and/or retro-Michael addition to the (sum of) isomers can be chosen within wide limits. Usually the ratio may be within the range of 0.00001:1 to 100:1, preferably in the range of 0.001:1 to 10:1, more preferably 0.01:1 to 0.5:1.

In an embodiment, isomerising conditions comprise exposure to light promoting isomerisation.

In particular a compound with Formula II

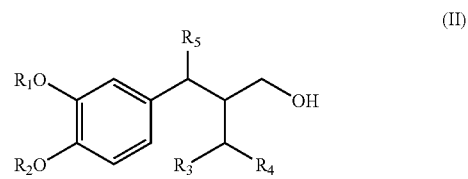

(II)

may be prepared by reducing the aldehyde of a compound according to Formula (IX), wherein $R_1$, $R_2$, $R_3$, $R_4$ and $R_5$ are as defined in claim 1, e.g. in a manner known per se for the reduction of aldehydes.

Preferably, the compound of Formula (II) is formed enantioselectively with respect to the R-isomer or the S-isomer, preferably wherein the R-isomer is prepared in excess of the S-isomer. More preferably, the preparation of a compound according to Formula (II) is carried out under conditions under which the compound according to Formula (IX) is racemizing.

To achieve racemization of a compound according to Formula (IX) any known method may be used. For example, the compound according to Formula (IX) is racemizing when additives selected from the group of acids or bases, preferably inorganic bases or secondary amines, are present during the reduction of the compound according to Formula (IX). Most preferably, secondary cyclic amines are used to achieve racemization, for example pyrrolidine.

The compound of Formula II can be converted to a compound according to Formula X,

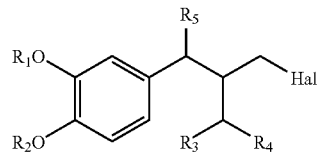
(X)

wherein $R_1$, $R_2$, $R_3$, $R_4$ and $R_5$ are as defined in claim 1 and "Hal" is a halogen atom, preferably Cl. This can be done by halo-dehydroxylation, e.g. based on a method described in Tetrahedon Letters 2000, 41, 10085-10089 and 10091-10094.

It is also possible to prepare compound X by converting the alcohol in a leaving group for instance an Alkylsulphonate, e.g. Methane sulphonate, and to substitute the leaving group with the halogen.

From compound (X), a compound with Formula (XI) can be made

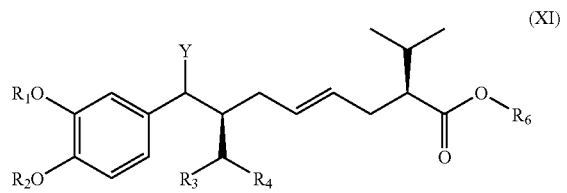
(XI)

wherein $R_1$, $R_2$, $R_3$ and $R_4$ are as defined in claim 1, Y is as $R_5$ in Formula (IX) and $R_6$ can be a hydrocarbon group or H, in particular H or $C_1$-$C_{12}$ alkyl, more in particular H or $C_1$-$C_6$ alkyl, preferably H, methyl or t-butyl, by reaction of a compound according to Formula (X) with a compound of Formula (XII)

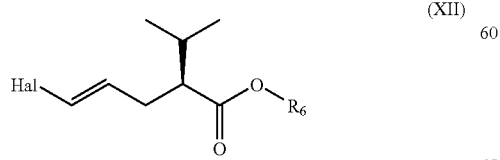
(XII)

wherein Hal is a halogen atom, preferably Cl.

This reaction can be carried out using a Grignard reagent, for instance comprising a metal moiety selected from the group of Mg, Zn or Li and a metal moiety selected from the group of Mn, Cu, Fe, Ni and Pd. Suitable conditions are, e.g., described in WO 02/02508.

Optionally the compound of Formula XI can be converted into a further compound, for instance based on a method as described in WO 02/02508.

In particular a compound according to Formula XIII can be made

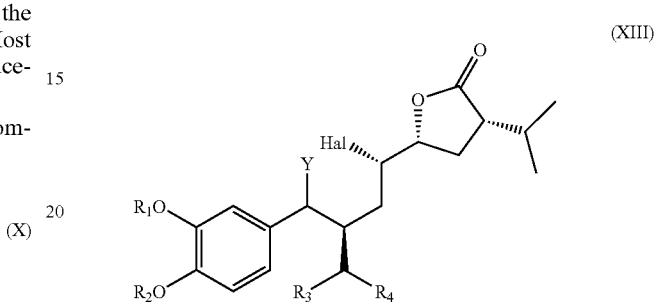
(XIII)

wherein $R_1$, $R_2$, $R_3$, $R_4$ and $R_5$ are as defined in claim 1, Hal is a halogen atom and Y corresponds to $R_5$. If Y is a hydrogen atom, halogenation and lactonisation can take place directly. Halogenation can be done using a halogenating agent, preferably a brominating agent, for instance N-bromosuccinimide. The reaction can for instance be carried out in dichloro methane or another suitable solvent.

In case Y is different from hydrogen, then usually Y will first be hydrolysed, for example by alkaline hydrolysis. For instance concentrated hydroxide (e.g. at least 30% NaOH or KOH) can be used. The compound may be precipitated with a base, for instance an amine, e.g. cyclohexylamine.

The compound of Formula XIII can be converted in a compound according to Formula XIV

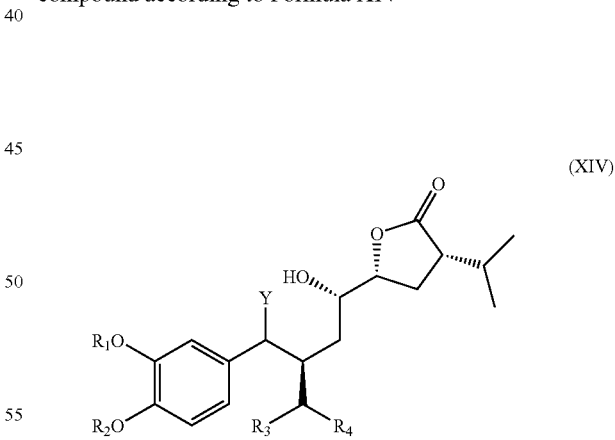
(XIV)

wherein $R_1$, $R_2$, $R_3$, $R_4$ and $R_5$ are as defined in claim 1 and Y corresponds to $R_5$, by substitution of the halogen by —OH. This can be accomplished in a solution comprising hydroxide, for instance an aqueous NaOH or KOH solution (e.g. about 1 M in water).

The compound of Formula XIV can be converted in a compound according to Formula XV

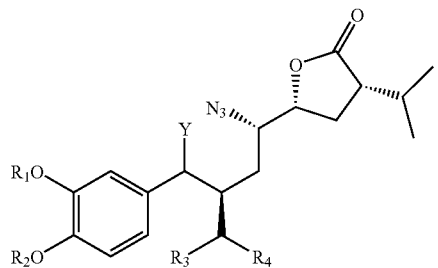

(XV)

wherein $R_1$, $R_2$, $R_3$, $R_4$ and $R_5$ are as defined in claim 1 and Y corresponds to $R_5$.

This can be accomplished by direct reaction with an activate azide, such as a metal azide. A preferred metal azide is sodium azide.

If desired, the compound of Formula XIV may first be converted to a compound according to Formula XIX

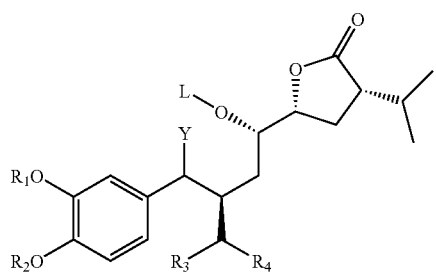

(XIX)

wherein $R_1$, $R_2$, $R_3$, $R_4$ and $R_5$ are as defined in claim 1 and Y corresponds to $R_5$ and L is a leaving group, for instance Alkyl-sulphonate, in particular $CH_3$—$SO_3$—. This reaction can be done with a salt of the leaving, for instance mesylate chloride, e.g. in triethylamine, in the presence of an amine.

Compound XIX can be reacted with azide.

The compound of Formula (XV) can be used to prepare a compound of Formula XVI,

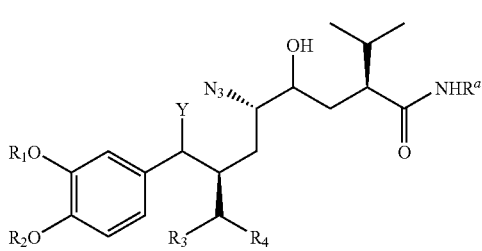

(XVI)

wherein $R_1$, $R_2$, $R_3$, $R_4$ and $R_5$ are as defined in claim 1 and Y corresponds to $R_5$ by reacting the compound of Formula XV with $H_2NR^a$, e.g. in triethylamide, in the presence of 2-hydroxypyridine. $R^a$ is H or optionally substitute hydrocarbon. The hydrocarbon optionally contains one or more heteroatoms. Preferably $R^a$ is —$(CH_2)_xCO$—$NH_2$ wherein x is 3-6, more preferably $R^a$ is —$CH_2$—$[CH(CH_3)_2]$—$CO$—$NH_2$.

Thereafter, the azide can be reduced with hydrogen gas, resulting in a compound according to Formula (XVII)

wherein $R_1$, $R_2$, $R_3$, $R_4$ and $R_5$ are as defined in claim 1, Y corresponds to $R_5$ and $R^a$ is as defined above, usually in the presence of a hydrogenation catalyst, for instance a Paladium catalyst, e.g. on a carbon support. This reaction may in particular be carried out in the presence of ethanolamine.

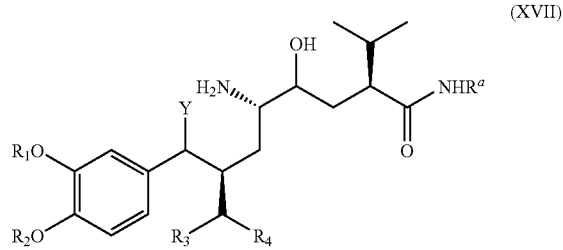

(XVII)

This hydrogenation can be carried out in the presence of an acid, e.g. fumaric acid, or the product may be mixed with an acid thereafter, to provide the corresponding salt.

The invention further relates to all possible combinations of different embodiments and/or preferred features according to the method according to the invention or the compound according to the invention as described herein.

EXAMPLES

Example 1

Preparation of a Compound of the Formula (I) (E/Z Mixture)($R_1$=3-methoxypropyl)

a) Preparation of pyrrolidino-3-methylbut-1-ene (enamine)

194 g (2.25 mol) of isovaleraldehyde are diluted in 1115 ml of toluene and cooled to 0° C. with stirring. 190.3 g (2.68 mol) of pyrrolidine, dissolved in 185.8 ml of toluene, were then added dropwise to this solution, such that the reaction temperature did not rise above 5° C. After the addition had ended, the reaction solution was stirred at 5° C. for another 1 hour. Subsequently, the mixture was warmed to room temperature and the water formed was removed completely by extraction with toluene. Thereafter, the solvent was removed by evaporation and the crude product (329.1 g; 95% of theory) was stored at 4° C. in a refrigerator.

b) Reaction of enamine with 4-methoxy-3-(3-methoxypropoxy)benzaldehyde (A1)

222.3 g (0.99 mol) of Al were diluted with 240 g of 2-propanol. 321.2 g (2.31 mol) of the enamine, prepared in example 1a, were added to this solution at room temperature with stirring. The reaction mixture was then heated to 80° C. and stirred at this temperature for 50 hours. In order to remove unreacted A1, the reaction mixture was extracted with 1170 ml of $NaHSO_3$ (40%) and 1365 ml of water for 30 minutes.

The excess of enamine was removed by distillation using a Rotavapor and entrained out with 2-propanol (40 mbar, 50° C.). After an aqueous extraction, 148.4 g of aldehyde according to formula I (51.2%) were isolated.

Example 2

Preparation of a Compound of the Formula (I) (E/Z Mixture) ($R_1$=methane sulfonyl)

60 g (394 mmol) of isovanillin were dissolved in 200 ml of DMF and cooled to 0° C. 120 g of $Et_3N$ were added and 63 g (550 mmol) of methane sulfonyl chloride were slowly added dropwise. Thereupon the reaction mixture was extracted with EtOAc and HCl and then rotated to dryness (60° C., 10 mbar). Yield 83 g mesylated isovanillin (92% of the theoretical yield).

83 g (360 mmol) of mesylated isovanillin were dissolved in 250 ml of DMF and 250 ml of toluene and, with stirring, reacted at 60° C. with 90 g (646 mmol) of enamine prepared according to Example 1a.

Thereupon the solvent was extracted using a rotary evaporator (Rotavapor).

Yield 70 g (65% of the theoretical yield).

Example 3

Preparation of 2-(3-(methoxypropoxy)-4-methoxybenzyl)-3-methylbutanal (a Compound According to Formula (IX)

A solution of 2-(3-(methoxypropoxy)-4-methoxybenzylidene)-3-methylbutanal (7.0 mmol, 74% E and 26% Z), tetrarhodium dodecacabonyl (0.14 mmol), (2R,3R)-(+)-2,3-Bis-(Diphenylphosphino)butane (R,R-Chiraphos, 0.63 mmol) and 300 ul triethylamine in toluene (75 ml) was transferred into an autoclave. The mixture was hydrogenated at 70-80° C. and 20 bar $H_2$. After 42 hr additional tetrarhodium dodecacabonyl (0.14 mmol) was added to complete the reaction in 62 hr. The mixture was concentrated to 3.5 g black oil and purified by flash chromatography (heptane/ethyl acetate=2/1). Yield=1.6 g yellow oil (74%).

$^1$H NMR (CDCl$_3$) δ 1.02 (d, J=3.4, 3H), 1.04 (d, J=3.4, 3H), 2.03-2.14 (m, 3H), 2.43-2.51 (m, 1H), 2.67-2.74 (dd, 1H), 2.89-2.96 (dd, 1H), 3.36 (s, 3H), 3.58 (t, J=6.1, 2H), 3.83 (s, 3H), 4.09 (t, J=6.5, 2H), 6.68-6.79 (ar, 3H), 9.68 (d, J=2.6, 1H).

$^{13}$C NMR δ 20.1, 20.3, 28.7, 30.0, 32.1, 56.5, 59.0, 60.1, 66.5, 69.7, 112.4, 114.7, 121.5, 132.6, 148.4, 149.9, 205.5

Example 4

Method of Preparation of 2-(3-(methoxypropoxy)-4-methoxybenzyl)-3-methylbutanol(A Compound According to Formula (IX) by 2-Electron Bioreduction of 2-(3-(methoxypropoxy)-4-methoxybenzylidene)-3-methylbutanal (A Compound According to Formula (I) with *E.Coli* Cells Expressing Enone Reductase (ER), Adding Glucose Dehydrogenase (GDH from *Bacillus megaterium* Purchased at Jülich Chiral Solutions) for Cofactor Recycle The example focuses on the production of enantio-enriched saturated aldehyde under isomerising conditions starting from the E/Z mixture of 2-(3-(methoxypropoxy)-4-methoxybenzylidene)-3-methylbutanal. 1,4 dithio-DL-threitol (DTT) is used as isomerisation catalyst.
Conditions:
Atmospheric pressure, 25° C., pH=7.5 (pH adjustment with NaOH)
Ingredients Needed:
2-(3-(methoxypropoxy)-4-methoxybenzylidene)-3-methylbutanal (149.4 mg oil, purity=95%, E/Z ratio=74/26), Potassium phosphate buffer 100 mM pH=7.5 (27 ml), NADP$^+$ (25 mg),
Cell free extract (prepared via sonification) of *E.coli* TOP10 cells expressing Enone Reductase P1 from *A. thaliana* (3 ml cell free extract, equivalent with 230 mg cell wet weight, 25% over-expression of total protein), glucose dehydrogenase (400 units), glucose (200 mg), 1,4 dithio-DL-threitol (DTT, 1 ml of 1M solution in water). All over-expression experiments were carried out following Invitrogen protocols at www.invitrogen.com for Gateway cloning.
Results:
After 24 hr 2-(3-(methoxypropoxy)-4-methoxybenzylidene)-3-methylbutanal conversion was >99%, closing the carbon balance as follows: >90% had been converted to the (R)-enantiomer of the corresponding saturated aldehyde (compound according to formula (IX)) (e.e.=82%), <10% was converted to the corresponding saturated alcohol (compound according to formula (II))(due to background ADH activity of *E.coli* cells).

Example 5

Method for the Preparation of 2-(3-(methoxypropoxy)-4-methoxybenzyl)-3-methylbutanol by 4-Electron Bioreduction of 2-(3-(methoxypropoxy)-4-methoxybenzylidene)-3-methylbutanol with *E.Coli* Cells Expressing Enone Reductase (ER), *E.Coli* TOP10 Cells Expressing Alcohol Dehydrogenase (ADH), Adding Glucose Dehydrogenase (GDH from *Bacillus megaterium* Purchased at Jülich Chiral Solutions) for Cofactor Recycle The example focuses on the production of enantio-enriched saturated alcohol under isomerising conditions starting from the E/Z mixture of 2-(3-(methoxypropoxy)-4-methoxybenzylidene)-3-methylbutanal. 1,4 dithio-DL-threitol (DTT) is used as isomerisation catalyst.
Conditions:
Atmospheric pressure, 25° C., pH=7.5 (pH adjustment with NaOH)
Ingredients Needed:
2-(3-(methoxypropoxy)-4-methoxybenzylidene)-3-methylbutanal (151.1 mg oil, purity=95%, E/Z ratio=74/26), Potassium phosphate buffer 100 mM pH=7.5 (27 ml), NADP$^+$ (25 mg),
Cell free extract (prepared via sonification) of *E.coli* TOP10 cells (purchased at Invitrogen) expressing Enone Reductase P1 (3 ml cell free extract, equivalent with 230 mg cell wet weight, 25% over-expression of total protein), cell free extract (prepared via sonification) of *E.coli* TOP10 cells expressing ADH E7 (1 ml cell free extract, equivalent with 80 mg cell wet weight, 30% over-expression of total protein), glucose dehydrogenase (400 units), glucose (200 mg), 1,4 dithio-DL-threitol (DTT, 1 ml of 1M solution in water). All over-expression experiments were carried out following Invitrogen protocols at www.invitrogen.com for Gateway cloning.
Results:
After 24 hr 2-(3-(methoxypropoxy)-4-methoxybenzylidene)-3-methylbutanal conversion was >99%, almost closing the carbon balance with the saturated alcohol (4-electron reduced product). As a result, >90% of the almost completely converted substrate had been converted to the (R)-enantiomer of the corresponding saturated alcohol (e.e.=82%).

Example 6

Preparation of 2-(3-(methoxypropoxy)-4-(2-(chloromethyl)-3-methylbutyl)-1-methoxybenzene (A Compound According to Formula (X)) from 2-(3-(methoxypropoxy)-4-methoxybenzyl)-3-methylbutanol (A Compound According to the Formula (II)

2-(3-(methoxypropoxy)-4-methoxybenzyl)-3-methylbutanol (45 g) was dissolved in toluene (52 mL) and triethylamine (16.9 g) was added as base. Next mesylchloride (13 mL) was added dropwise at room temperature and the reaction mixture was stirred for 30 minutes to complete the mesylating reaction. After the conversion was completed, DMF (47 mL), and sodiumchloride (17.6 g) were added to the reaction mixture and the mixture was heated to 100-120° C. for 2 hr. Na-mesylate was obtained as by-product.

The reaction mixture was cooled to 50° C., and at this temperature the reaction mixture was twice extracted with $H_2O$ (150 and 100 mL, respectively). The toluene layer was treated with 0.9 g of active coal, filtered, and evaporated. The residue was dissolved in 2-Propanol (115 mL) at 50° C., filtered, and cooled to −10° C. (cooling process in total is 8 hr). The crystals were isolated by filtration, washed with cold 2-Propanol (−10° C.)(2 times 45 mL) and dried at 35° C. under vacuum conditions (5 mbar). Yield: 39 g (82%) of 2-(3-(methoxypropoxy)-4-(2-(chloromethyl)-3-methylbutyl)-1-methoxybenzene.

The invention claimed is:

1. Compound according to Formula (IX)

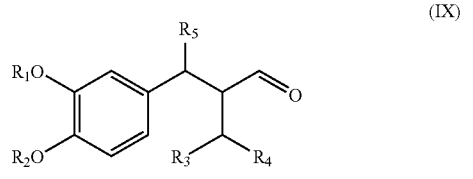

(IX)

and salts thereof,
wherein $R_1$ and $R_2$ are each independently selected from H and hydrocarbon moieties, which hydrocarbon moieties optionally comprise one or more heteroatoms, and which hydrocarbon moieties optionally comprise substituents, or when the compound according to formula (IX) is a salt, $R_1$ and/or $R_2$ may be a cation,
$R_3$ and $R_4$ each independently are selected from the group of $C_1$-$C_6$ alkyl and $R_5$ is selected from H, $C_1$-$C_6$ alkoxyls, tri($C_1$-$C_6$ alkyl)silyls, $C_1$-$C_6$ alkyls, and wherein $R_1$ and $R_2$ are optionally linked together to form a ring structure.

2. Compound according to claim 1, wherein $R_1$ is H, alkoxy-alkyl or an oxygen protective group, $R_2$ is hydrogen, alkyl or an oxygen protective group, $R_3$ and $R_4$ are each independently methyl and $R_5$ is H.

3. Compound according to claim 1, wherein $R_1$ is 3-methoxy-propyl and $R_2$ is $C_1$-$C_6$ alkyl, $R_3$ and $R_4$ are each independently methyl and $R_5$ is H.

4. Compound according to claim 1, wherein the compound is selected from the group of
2-(3-(3-methoxypropoxy)-4-methoxybenzyl)-3-methylbutanal,
2-(3-(3-methoxypropoxy)-4-hydroxybenzyl)-3-methylbutanal,
2-(3-methoxypropoxy)-4-(2-formyl-3-methylbutyl)phenyl tolylsulfonate,
2-(3-methoxypropoxy)-4-(2-formyl-3-methylbutyl)phenyl benzoate,
2-(3,4-dihydroxybenzyl)-3-methylbutanal,
2-(3-trimethylsilylhydroxy)-4-methoxybenzyl)-3-methylbutanal.

5. Method for preparing a compound of Formula (IX) according to claim 1, comprising converting the α,β carbon-carbon unsaturation of an E-isomer, a Z-isomer or a mixture of an E-isomer and a Z-isomer of a compound according to Formula (I)

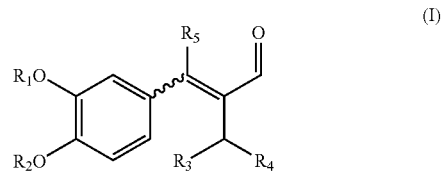

(I)

wherein the conversion takes place in the presence of a catalytic amount of an enzyme selected from the group of oxidoreductases, in particular from the group of ene reductases;
the conversion of the α,β carbon-carbon unsaturation of an E-isomer, a Z-isomer or a mixture of an E-isomer and a Z-isomer of a compound according to Formula (I) is carried out under isomerising conditions, said isomerising conditions preferably comprising the presence of a compound capable of participating in a Michael addition and a retro-Michael addition, more preferably in the presence of a compound selected from the group of thiols, including thioalkohols; halogens; secondary amines; and tertiary amines; and
wherein $R_1$ is 3-methoxypropyl, $R_2$, is methyl, $R_3$, is methyl, $R_4$ is methyl and $R_5$ is H.

* * * * *